United States Patent [19]
Kawano

[11] Patent Number: 5,233,993
[45] Date of Patent: Aug. 10, 1993

[54] ULTRASONIC DIAGNOSTIC APPARATUS AND IMAGE FORMING METHOD THEREFOR

[75] Inventor: Toshihiko Kawano, Nagareyama, Japan

[73] Assignee: Hitachi Medical Corporation, Chiyoda, Japan

[21] Appl. No.: 794,049

[22] Filed: Nov. 19, 1991

[30] Foreign Application Priority Data

Nov. 19, 1990 [JP] Japan .................................. 2-311523

[51] Int. Cl.$^5$ .............................................. A61B 8/00
[52] U.S. Cl. .................... 128/660.07; 128/661.01
[58] Field of Search ................. 128/660.01, 660.06, 128/660.07, 661.03, 661.04, 661.09

[56] References Cited

U.S. PATENT DOCUMENTS

| | | | |
|---|---|---|---|
| 4,790,321 | 12/1988 | Miwa et al. ................... | 128/660.07 |
| 4,817,619 | 4/1989 | Sugiyama et al. ............. | 128/661.09 |
| 4,888,694 | 12/1989 | Chesarek .................... | 128/660.01 X |
| 5,060,515 | 10/1991 | Konda et al. ............... | 128/660.01 X |
| 5,109,857 | 5/1992 | Roundhill et al. .......... | 128/660.07 X |
| 5,111,823 | 5/1992 | Cohen ......................... | 120/660.07 |

FOREIGN PATENT DOCUMENTS 61-89054 8/1987 Japan .

OTHER PUBLICATIONS

Höhne, K. "Digital Image Processing in Medicine" Springer-Verlag N.Y., N.Y. pp. 1-10 and 197.

*Primary Examiner*—Francis Jaworski
*Attorney, Agent, or Firm*—Antonelli, Terry, Stout & Kraus

[57] ABSTRACT

An ultrasonic diagnostic apparatus operates such that the ultrasonic beam transmission and reception is made in the same scanning direction twice at intervals shorter than the frame rate. A subtraction operation is performed between line data obtained by the successive transmissions and receptions. A subtraction image is formed by subtraction image data obtained by scanning in a plurality of scanning directions.

19 Claims, 10 Drawing Sheets

ULTRASONIC DIAGNOSTIC APPARATUS AND IMAGE FORMING METHOD THEREFOR

BACKGROUND OF THE INVENTION

This invention relates to an ultrasonic diagnostic apparatus for extracting and displaying the motion component of the examined region of an examined body (patient), for example, a locomotive region such as a blood vessel or the heart by utilizing an ultrasonic beam, and more particularly to an ultrasonic diagnostic apparatus for displaying both said locomotive regions which move quickly and which move slowly in an easily observable state.

As described in JP-A-62-189054, a conventional ultrasonic diagnostic apparatus of this kind comprises a beam transmission/reception unit (a probe and an ultrasonic beam transmission/reception unit) for transmitting and receiving an ultrasonic beam to and from the examined body, a tomographic scanning unit for obtaining tomographic image (B-mode image) data about the examined body including the locomotive regions repeatedly at specified intervals by using reflected echo signals from the ultrasonic beam transmission/reception unit, a unit (subtraction processor) for calculation between time-series images obtained by the tomographic scanning unit, and an image display device (TV monitor) for displaying subtraction image data from the subtraction image data generating unit.

Therefore, from the reflected echo signals from the ultrasonic beam transmission/reception unit, tomographic image data of the examined body, including the locomotive regions is obtained by the tomographic scanning unit repeatedly at specified intervals, calculation is performed between time-series images obtained by the tomographic scanning unit to generate subtraction image data, and the subtraction image data is displayed on the image display device.

In this case, in said time-series images, if the locomotive region in the examined body moves in a time space from when an image is obtained in the previous scanning until an image is obtained in the current scanning, a difference occurs in the image data between the previous and current images of the region that moved. The image data on those two images is the same for the regions which have been stationary and subtraction data is zero, so that only that locomotive region is displayed.

In such a conventional ultrasonic diagnostic apparatus, however, two completed tomographic images of different time phases are taken out, a subtraction operation is performed between images generate subtraction image data, and a subtraction image is displayed. Therefore, the time required for subtraction depends on the frame rate of image display. For example, in the case of 30 frames/sec, if a subtraction operation is performed between two successive images, the time for subtraction is about 33 ms, and if subtraction is performed between images separated by one image, the subtraction time is about 66 ms, and if subtraction is performed between images separated by two images, the subtraction time is about 99 ms.

In this case, as the time interval between two tomographic images subjected to a subtraction operation increases, the amount of displacement of the movement of the fast-moving locomotive region increases, so that the detailed movement of that locomotive region cannot be observed in detail. Conventionally, when the shortest time interval is selected, the subtraction time is about 33 ms. But with the fast-moving regions, such as the valves or walls of the heart, this time interval is still so long that the movement of the region at issue cannot sometimes be observed in detail. In order to observe the high-speed locomotive region such as the valves and walls of the heart, the subtraction time is preferably about 10 ms at the frame rate of about 100 frames/sec. However, such a fast imaging is impossible with ordinary ultrasonic diagnostic apparatuses.

On the other hand, with the slow-moving locotomive regions in which their amounts of displacement is small, when the subtraction time is very short, the moving condition can hardly be observed. In this case, it is necessary to elongate the subtraction time adequately to make their moving condition observable.

SUMMARY OF THE INVENTION

In present invention, it is an object to provide an ultrasonic diagnostic apparatus which solves the above problems and which can display both fast-moving and slow-moving tissue in an easily observable state.

To achieve the above object, the ultrasonic diagnostic apparatus according to the present invention comprises an ultrasonic beam transmission/reception unit for transmitting and receiving an ultrasonic beam to and from the examined body, a tomographic scanning unit for obtaining tomographic image data of the examined body including the locomotive region repeatedly at specified intervals by using reflected echo signals from the ultrasonic beam transmission/reception unit, a unit for calculation between data of different time phases obtained by the tomographic scanning unit and generating subtraction image data, and an image display device for displaying subtraction image data from the subtraction image data generating unit. In the present ultrasonic diagnostic apparatus, the tomographic scanning unit includes a circuit for delaying, for a specified time, line data of a previous time phase among the line data obtained by scanning, or transmitting and receiving the ultrasonic beam twice in he same transmitting direction of the ultrasonic beam and sends the line data of two successive time phases to the subtraction image data generating unit.

In another case according to the present invention, all of the scanning directions are divided into a plurality of groups each of which consist of a plurality of scanning directions. In this case, the scanning is performed at every groups. In this case, the above-mentioned tomographic scanning unit may include a circuit for delaying, for a specified time, line data of a previous time phase among the line data obtained by scanning, or transmitting and receiving the ultrasonic beam twice in the same scanning direction.

In the present invention, the interval between two times of successive transmission and reception of an ultrasonic beam in the same scanning direction can be set at an optional value in units of time required for one time of transmission and reception of the ultrasonic beam. For observation of the fast-moving tissue, the interval between transmission and reception is set at a small value, and for observation of the slow-moving tissue, the interval is set at a large value.

In addition, the movement of the locomotive region can be more clearly understood because the subtraction image can be observed, while comparing it with an ordinary tomographic image. On the output side of subtraction image data generating unit, a selecting unit is provided. The effecting unit is for receiving tomographic image data and subtraction image data, and for selecting and for outputting either the tomographic image data or the subtraction image data in synchronism with display intervals of the image display device in order to simultaneously display a tomographic image and a subtraction image in the same picture.

It is also possible to provide a tomographic image storage device on the output side of the tomographic scanning unit, a subtraction image storage device on the output side of the subtraction image data generating unit, and a selection unit at the stage following those storage devices. In this case, an image constructed on the basis of the image data from the selection is displayed. The image is divided by an optional straight line, so that a tomographic image is displayed on one side and a subtraction image is displayed on the other side.

Moreover, the movement of the locomotive region is clearly observed, if tomographic and subtraction images of the same time phase are displayed side by side in the same picture of the image display device by providing a line memory with a capacity for data corresponding to one horizontal scanning line of the image display device for each of the tomographic image storage device and the subtraction image storage device, and the line memories arranged at the stage preceding the selection unit and following the storage devices.

It is possible to provide at a stage just following the subtraction image storage device a unit for converting subtraction image data into color information and a unit for superposing colored subtraction image data on tomographic image data from the tomographic image storage device and for sending the data to the image display unit. By doing so, the change in the movement of the locomotive region can be easily understood because the region at issue is shown in color on a monochrome tomographic image.

In the ultrasonic diagnostic apparatus arranged as described, among the line data obtained by scanning twice in the same direction in which the ultrasonic beam is transmitted, the line data of the preceding time phase is delayed for a specified time, and the line data of two successive phases are sent to the subtraction data generating unit. Therefore, the subtaction image data generating unit receives the line data of two successive time phases sent out by the tomographic scanning unit, and can generate subtraction image data from data obtained by scanning in the direction of each scanning line. Accordingly, the subtraction time for forming a subtraction image can be controlled for respective sets of scanning lines, so that the number of scanning lines is reduced for observing a fast-moving locomotive region or increased for observing a slow-moving locomotive region. As a result, the locomotive regions can be shown in an easily observable state.

DESCRIPTION OF THE PREFERRED EMBODIMENTS

Embodiments of the present invention will be described with reference to the accompanying the drawings.

Figure 1:
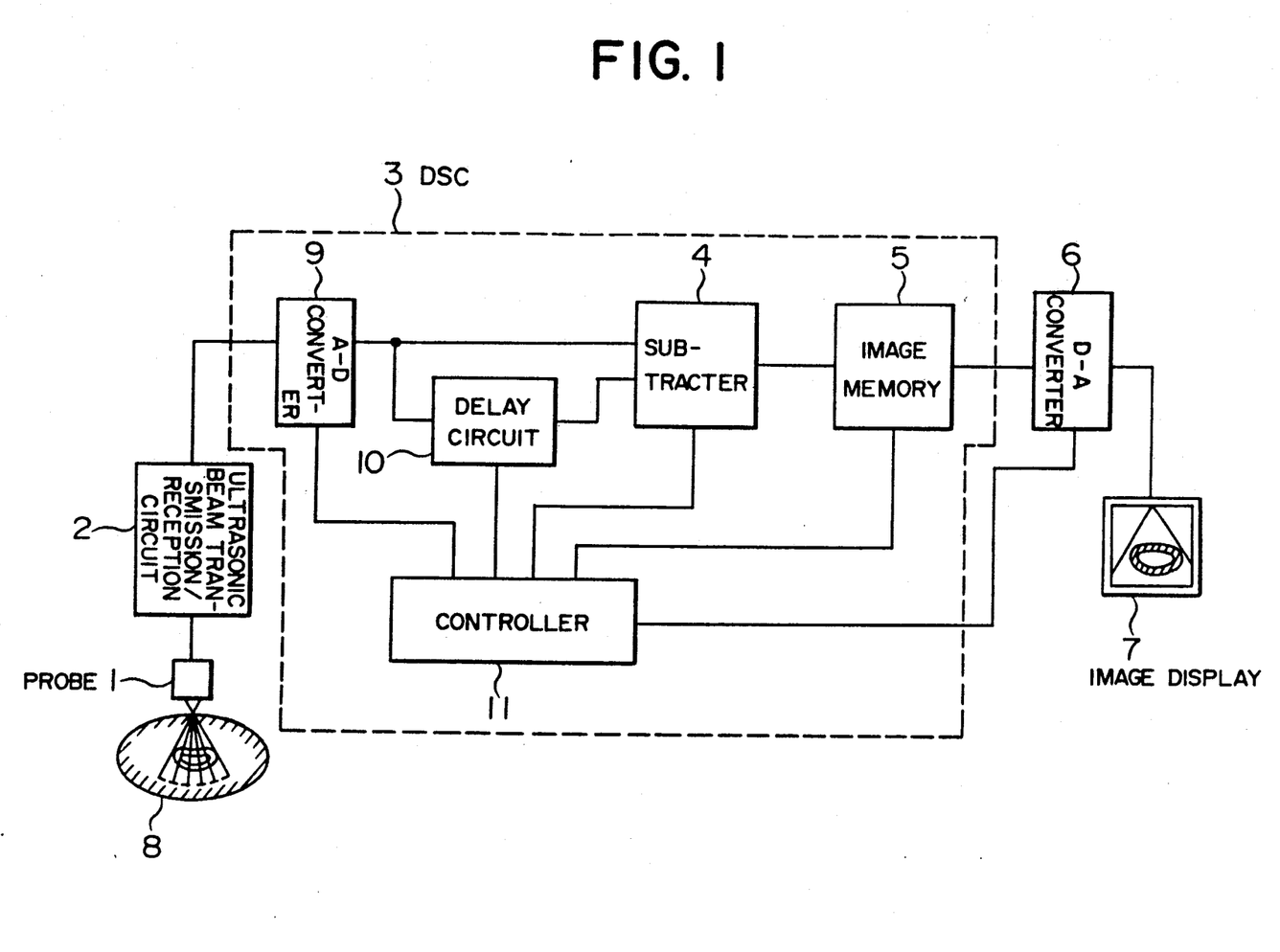
FIG. 1 is a block diagram showing a first embodiment of the ultrasonic diagnostic apparatus according to the present invention.

FIG. 1 is a block diagram showing a first embodiment of an ultrasonic diagnostic apparatus according to the present invention. This ultrasonic diagnostic apparatus is capable of extracting and displaying the motion component of the examined region of the examined body, particularly the locomotive regions such as the blood vessels and the heart, by utilizing an ultrasonic beam. As shown in FIG. 1, the apparatus comprises a probe 1, an ultrasonic beam transmission/reception circuit 2, a digital scan converter (hereafter referred to as "DSC") 3, a D-A converter 6, and an image display 7.

The probe 1 transmits and receives an ultrasonic beam to and from the examined body 8 while performing beam scanning of the body mechanically or electronically. Although not shown in the figure, the probe 1 includes a transducer which generates an ultrasonic beam and receives the reflected echo. The ultrasonic beam transmission/reception circuit 2 sends drive pulses to the probe 1 to cause it to generate the ultrasonic beam and processes the reflected echo signals supplied. Though not shown, the ultrasonic beam transmission/reception circuit 2 contains a transmission pulser, a transmission delay circuit, a reception amplifier, a reception delay circuit, and an adder. The ultrasonic beam transmission/reception unit, which is formed by the probe 1 and the ultrasonic beam transmission/reception circuit 2, obtains a tomographic image by scanning the ultrasonic beam inside of the examined body in a predetermined direction.

The DSC 3 serves as a tomographic scanning unit for obtaining data representing tomographic images of the inside of the examined body including the locomotive regions in accordance with the ultrasonic beam transmission intervals by using reflected echo signals supplied by the ultrasonic beam transmission/reception circuit 2, reads out the data for display in synchronism with the TV operation, and also controls the system. The DSC 3 comprises an A-D converter for converting the reflected echo signal from the ultrasonic beam transmission/reception circuit 2 into digital signals, a delay circuit 10 which is a feature of the present invention, a subtracter 4, an image memory 5, and a controller 11 for controlling the operation of these components.

The subtracter 4 is a unit for calculation between data of different time phases obtained by the ultrasonic beam transmission/reception circuit 2 and generating subtraction image data, and performs subtraction between data from the delay circuit 10 and data newly supplied from the A-D converter 9. The subtracter 4 is formed, for example, by using a standard logic.

The image memory 5 stores image data for one frame by receiving subtraction image data from the subtracter 4, and operates synchronized with an image display device which is described later. The D-A converter 6 converts the subtraction image data supplied from the image memory 5 into analog signals. The image display 7 consists of, for example, a TV monitor, and receives a video signal from the D-A converter 6 and displays an image. The image display 7 and the D-A converter constitute an image display device.

In this invention the delay circuit 10 in the DSC 3 delays one line of data of the former time phase among two items of line data obtained by two successive scannings in the same beam transmitting direction. More specifically, the delay circuit 10 operates such that digital signals from the A-D converter 9 are written into and read from the line memory for every scanning line of the ultrasonic beam. This read/write process is repeated, and the delay circuit 10 is formed by a semiconductor memory. In parallel with the delay circuit 10, a data line extends from the output terminal of the A-D converter 9, and is connected to another input of the subtracter 10. Consequently, two items of the line data of two successive time phases are supplied sequentially from the delay circuit 10 and the A-D converter 9 to the subtracter 4.

Description will now be made of the ultrasonic diagnostic apparatus constructed as described with reference to FIGS. 2 and 3. The probe 1 shown in FIG. 1 is brought into contact with the position of the examined body 8 which corresponds to the examined region, and the ultrasonic beam is transmitted to the examined region. The ultrasonic beam transmitted from the probe 1 is converged to form a thin beam on the examined region by a transmitting delay circuit in the ultrasonic beam transmission/reception circuit 2. This transmitted beam is reflected by the examined region and becomes a reflected echo. The echo is received by the probe 1, and taken through the reception amplifier, reception delay circuit and adder in the ultrasonic beam transmission/reception circuit 2, so that a received beam is formed. The probe 1 repeatedly transmits and receives the ultrasonic beam by sequentially changing the beam-transmitting/receiving direction at specified intervals, and thereby the examined region is scanned.

The reflected echo signal supplied from the ultrasonic beam transmission/reception circuit 2 is input to the A-D converter 9 in the DSC 3 and is converted into a digital signal. As shown in FIG. 2, successive transmissions and receptions are performed in the same direction and by repeating this process, the ultrasonic beam is sequentially transmitted and received in each scanning direction. For example, scanning ① and scanning ② are performed successively in the direction of the first scanning line $L_1$, then scanning ③ and scanning ④ are performed successively in the direction of the second scanning line $L_2$, and then scanning ⑤ and scanning ⑥ are performed in the direction of the third scanning line $L_3$. In this manner, two successive scannings are performed in the respective directions of the scanning lines $L_1$ to $L_n$ under control by the controller 11. Transmission of the ultrasonic beam is executed synchronized with a transmission timing signal T shown in FIG. 3(a). Two successive transmissions and receptions are performed at each line address in each of the directions of scanning lines $L_1$ to $L_n$.

Figure 3:
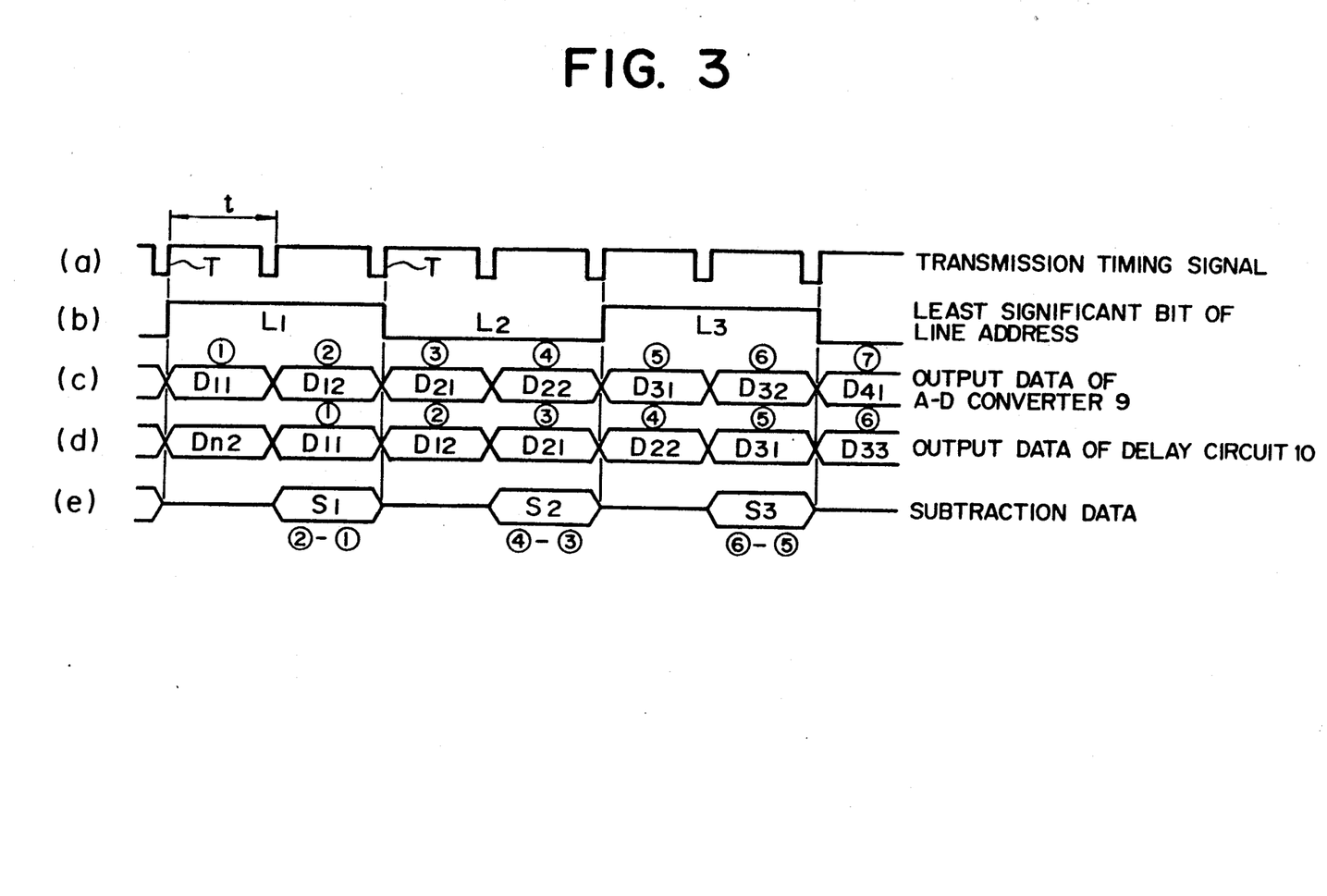
FIG. 3 is a timing chart for explaining the operation of generating subtraction image data in FIG. 1.

Referring to data which has been converted into a digital signal by the A-D converter 9, as shown in FIG. 3(c), data $D_{11}$ and $D_{12}$ are output for the first scanning line $L_1$, then data $D_{21}$ and $D_{22}$ are output for the second scanning line $L_2$, and next, data $D_{31}$ and $D_{32}$ are output for the third scanning line. Data is obtained in this manner. Those data are then sent to the delay circuit 10 and the subtracter 4. Each item of data input into the delay circuit 10 is delayed for a time of one time interval of transmission and reception of the ultrasonic beam by the control of the controller 11. Therefore, data output from the delay circuit 10 are respectively delayed by a period of time corresponding to one transmission timing signal T with respect to data output from the A-D converter 9. In other words, the line data of the former time phase is delayed among two items of line data obtained by two-time scanning in each of the scanning lines $L_1$ to $L_n$.

Under this condition, output data from the A-D converter 9 and output data from the delay circuit 10 are respectively input into the inputs of the subtracter 4. Namely, two items of line data of two successive time phases are input. Then, as shown in FIG. 3(e), the subtracter 4 performs a subtraction operation between the two items of the line data during the second scanning in a direction of each of the scanning lines $L_1$ to $L_n$ by the control of the controller 11, and generates subtaction data. For example, for the first scanning line $L_1$, a difference is calculated between line data $D_{12}$ of the current time phase supplied from the A-D converter 12 and line data $D_{11}$ of the preceding time phase supplied from the delay circuit 10, and subtraction data $S_1$ is output. Then, for the second scanning line $L_2$, a difference is calculated between line data $D_{22}$ of the current time phase and line data $D_{21}$ of the preceding time phase, and subtraction data $S_2$ is output. Further, for the third scanning line $L_3$, a difference is calculated between line data $D_{32}$ of the current time phase and line data $D_{31}$ of the preceding time phase, and subtraction data $S_3$ is output.

Figure 2:
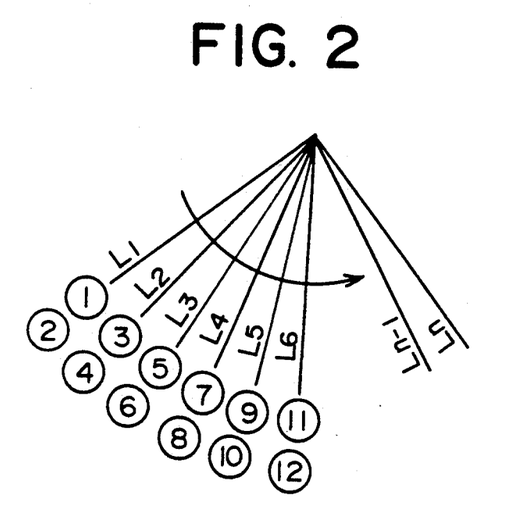
FIG. 2 is an explanatory diagram showing the operation of sequentially scanning an ultrasonic beam in the direction of each scanning line by repeating two times of successive transmission and reception in each direction.

In the manner described, subtraction data are generated sequentially up to the n-th scanning line $L_n$, and subtraction data are written in the image memory 5 in its storage areas corresponding to the scanning lines $L_1$ to $L_n$ as shown in FIG. 2, and thereby subtraction image data for one place of image is generated. In this case, as is clear from FIG. 3, assuming that a diagnosis depth is 20 cm, subtraction time t for forming a subtraction image becomes 260 μs because one scanning time in the direction of each scanning line for a diagnosis depth of 1 cm is 13 μs. Therefore, this is effective when observing a fast-moving locomotive region.

Then, subtraction image data is read from the image memory 5, and the data is converted into an analog video signal by the D-A converter 6. Subsequently, the video signal is input to the image display 7 and is displayed as a subtraction image. The subtraction image at this time is formed such that subtraction data obtained between the two items of the line data of the two successive time phases is arranged in each of the scanning lines $L_1$ to $L_n$. Therefore, in each scanning line direction, if the tissue of the examined region in the examined body moves during a time from when line data of the preceding time phase is taken until line data of the current time phase is taken, a difference occurs between the two items of the image data on a portion that moved between the preceding and current time phases. On the other hand, for a portion that has been stationary, the image data remains unchanged between the two time phases, and subtraction data is zero, so that only the locomotive region is displayed but nothing is shown of the stationary tissue. The subtraction image on the image display is only the portion that moved from when line data of the preceding time phase is taken until line data of the current time phase is taken.

By successively displaying images obtained by repetition of the above operation on the image display 7, a real-time picture of only the locomotive tissue of the examined region can be obtained.

If this embodiment is applied to, for example, a conventional apparatuses in which the frame rate of tomographic scanning is about 30 frames/sec (corresponding to an echo signal intake depth of 20 cm and about 100 ultrasonic scanning lines), when subtraction images are to be obtained at this depth, a total number of times of the transmission and reception to obtain subtraction images for one frame becomes twice as many, because the transmission and reception are carried out twice in the same direction. In natural consequence, the frame rate for subtraction image display is reduced to about 15 frames/sec and the image is likely to flicker. Therefore, to increase the frame rate even a little, a conceivable method is to narrow the subtraction image display area to some extent, i.e. by limiting the number of ultrasonic scanning lines to 80, 60 or 50, thereby preventing the frame rate from decreasing.

Figure 8:
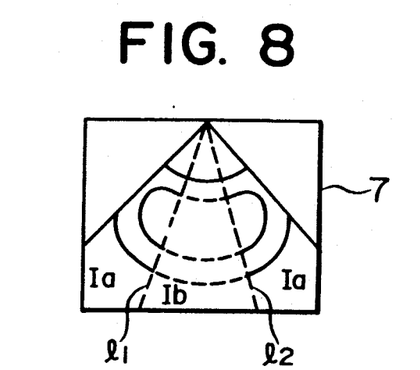
FIG. 8 is an explanatory diagram showing an example of image display in the third embodiment.

As shown in FIG. 8, among the 100 ultrasonic scanning lines $L_1$ to $L_{100}$ to produce a tomographic image, the scanning technique in this embodiment can be partially applied only to a range of 50 lines $L_{25}$ to $L_{75}$ in order to obtain subtraction images of only the region of interest.

Figure 4:
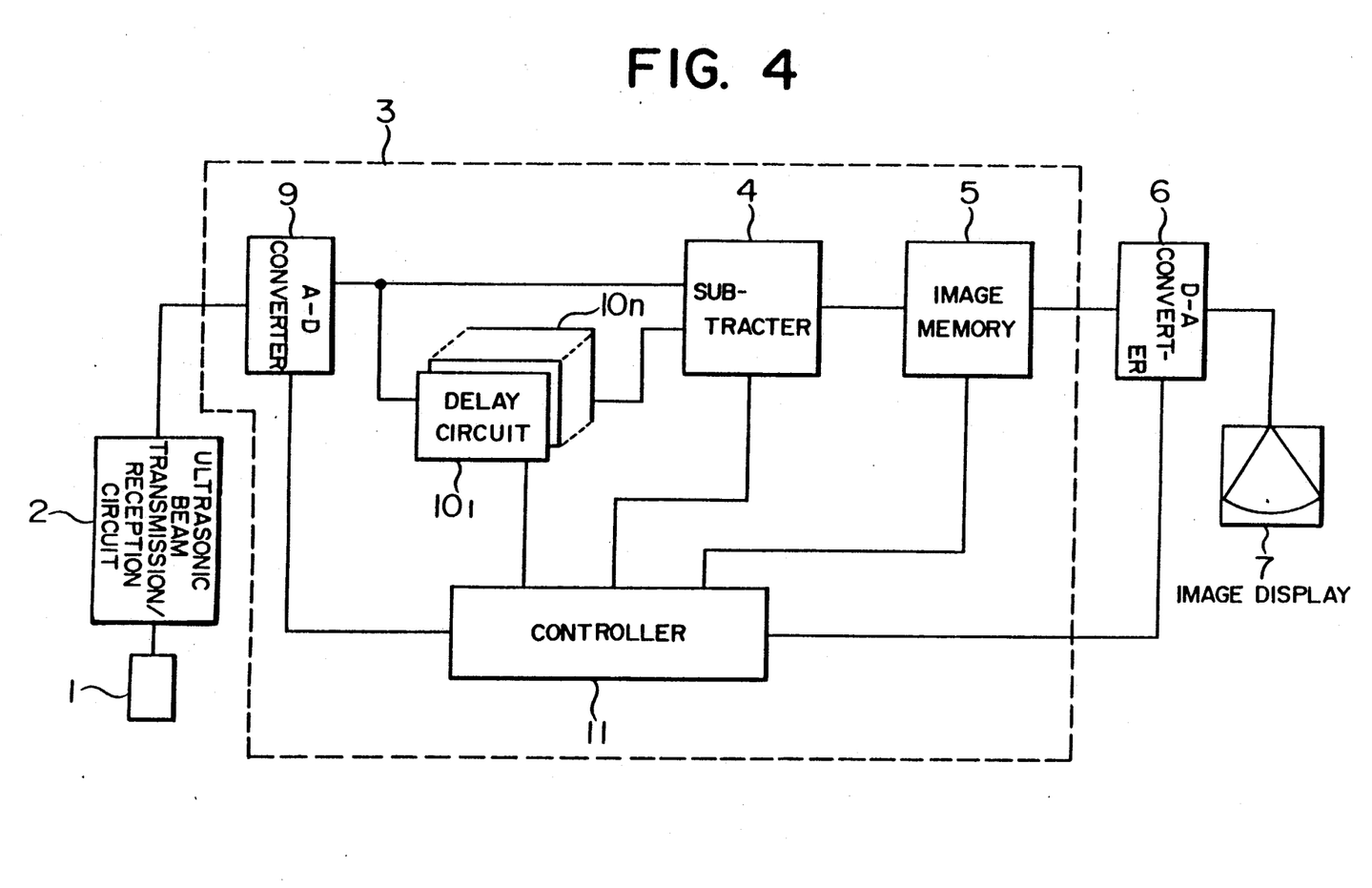
FIG. 4 is a block diagram showing a second embodiment of the present invention.
Figure 5:
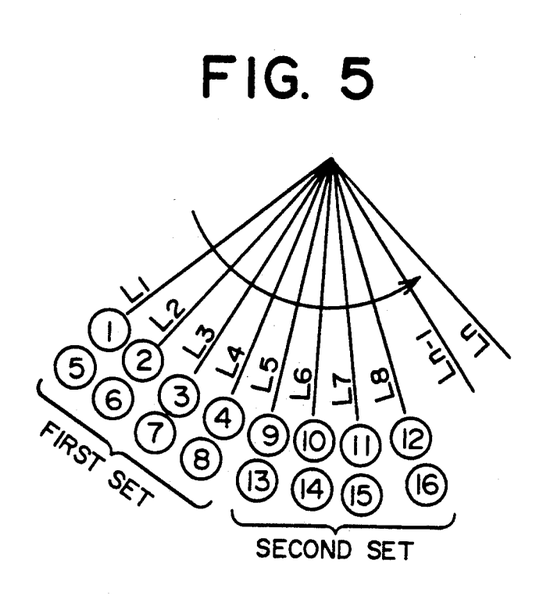
FIG. 5 is an explanatory diagram showing the operation of two times of successive transmission and reception of an ultrasonic beam in each scanning direction when every two or more directions in which the ultrasonic beam is transmitted are grouped as one set.

FIG. 4 is a block diagram showing a second embodiment of the present invention. In the second embodiment, every two or more ultrasonic beam transmitting directions are grouped as one set, two items of the line data is obtained by scanning twice in each direction. The former line data is delayed for a specified time by delay circuits $10_1$ to $10_n$ which correspond to the number of the ultrasonic beam transmitting directions in one set mentioned above. In this case, as shown in FIG. 5, every four scanning line directions are grouped as one set, from the first scanning line $L_1$ to the fourth scanning line $L_4$ and from the fifth scanning line $L_5$ to the eighth scanning line $L_8$, and so on, for example, and the transmission and reception are performed twice in the same scanning direction; therefore, four delay circuits $10_1$ to $10_4$ are required.

The operation of generating subtraction image data in the second embodiment will be described referring to FIGS. 5 and 6. In FIG. 5, the scanning lines $L_1$ to $L_4$ are designated as the first set, and the scanning of ①, ②, ③ and ④ is performed sequentially from the first scanning line $L_1$ to the fourth scanning line $L_4$. Then, returning once again to the first scanning line $L_1$, the ultrasonic beam of the subsequent time phase is made to traverse sequentially in the directions of ⑤, ⑥, ⑦ and ⑧ from the first scanning line $L_1$ to the fourth scanning line $L_4$. The transmission of the ultrasonic beam is controlled by the least significant bits ((d) in FIG. 6) of line addresses synchronized with the transmission timing signal T shown in FIG. 6(a). In a set of scanning lines $L_1$ to $L_4$, the repetition of the transmission and reception is controlled by the state of the next bits of the line addresses shown in FIG. 6(c). The above-mentioned operations are controlled by the controller 11.

Figure 6:
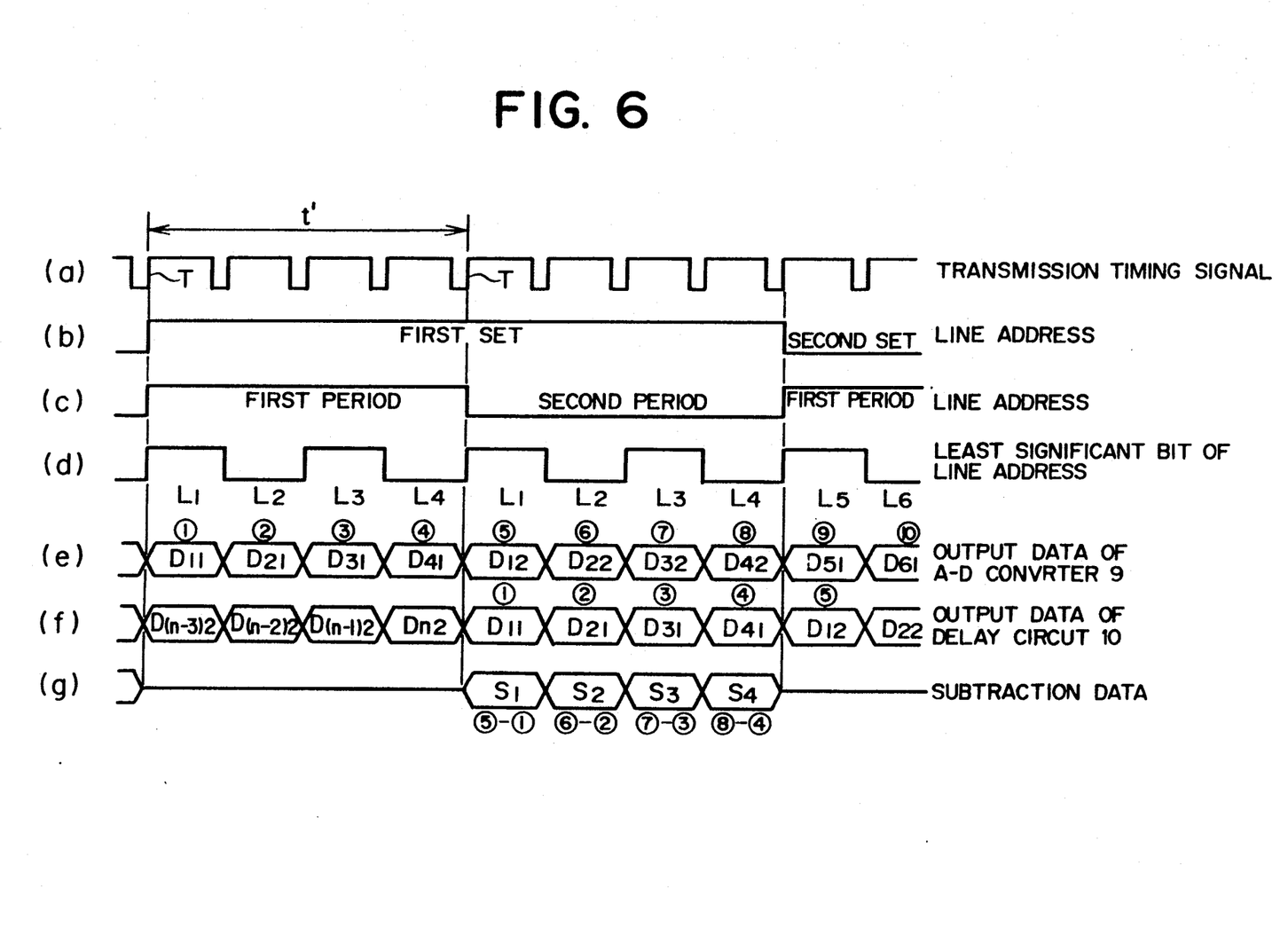
FIG. 6 is a timing chart for explaining the operation of generating subtaction image data in FIG. 4.

Referring to the digital signal supplied from the A-D converter 9, as shown in FIG. 6(e), in the first set of scanning lines, data is output sequentially for the scanning lines, namely, data $D_{11}$ for $L_1$, data $D_{21}$ for $L_2$, data $D_{31}$ for $L_3$, and data $D_{41}$ for $L_4$. Again, for the first set of scanning lines, data by the second scanning is output sequentially, namely, data $D_{12}$ for $L_1$, data $D_{22}$ for $L_2$, data $D_{32}$ for $L_3$, and data $D_{42}$ for $L_4$. Those data are sent to the delay circuits $10_1$ to $10_4$ and the subtracter 4. Specifically, data $D_{11}$ is input to the first delay circuit $10_1$, data $D_{21}$ to the second delay circuit $10_2$, data $D_{31}$ to the third delay circuit $10_3$, and data $D_{41}$ to the fourth delay circuit $10_4$. Data $D_{12}$ obtained by the second scanning is input to the first delay circuit $10_1$, data $D_{22}$ to the second delay circuit $10_2$, data $D_{32}$ to the third delay circuit $10_3$ and data $D_{32}$ to the fourth delay circuit $10_4$. Data input into the delay circuits $10_1$ to $10_4$ are respectively delayed by a period of time corresponding to four of successive transmissions and receptions of the ultrasonic beam by the controller 11. Therefore, data output from the A-D converter 9 are respectively delayed by a period of time corresponding to four transmission timing signal T. In other words, among the line data of the set of scanning lines $L_1$ to $L_4$ obtained by the two times of the successive transmission and reception in each scanning direction, the line data of the preceding time phase are delayed by a specified period of time.

Under this condition, output data from the A-D converter 9 and separate items of the output data from the delay circuits $10_1$ to $10_4$ are input to the inputs of the subtractor 4. In the subtracter 4, as shown in FIG. 6(g), under control by the controller 11, subtraction operations are performed between the two items of the line data of the two subsequent time phases for each scanning direction, and thereby the subtraction data $S_1$, $S_2$, $S_3$ and $S_4$ are generated.

In the manner described, subtraction data are generated for the respective scanning lines, grouped as separate sets arranged between the first scanning line $L_1$ to the n-th scanning line $L_n$, and as the data are written into the storage areas corresponding to the scanning lines $L_1$ to $L_n$ in the image memory 5, subtraction image data for one frame is prepared. In this case, subtraction time t' for forming a subtraction image is the time during the first scanning period for the scanning lines $L_1$ to $L_4$ of the first set as shown in FIG. 6. Therefore, when observing a slow-moving locomotive region, if a large value is set for t', the movement of the region of interest can be observed easily. In this second embodiment, as in the modification of the first embodiment, among the 100 ultrasonic scanning lines $L_1$ to $L_{100}$ for tomographic inspection, the scanning technique of the second embodiment may be partially applied to 50 lines $L_{25}$ to $L_{75}$, for example.

Figure 7:
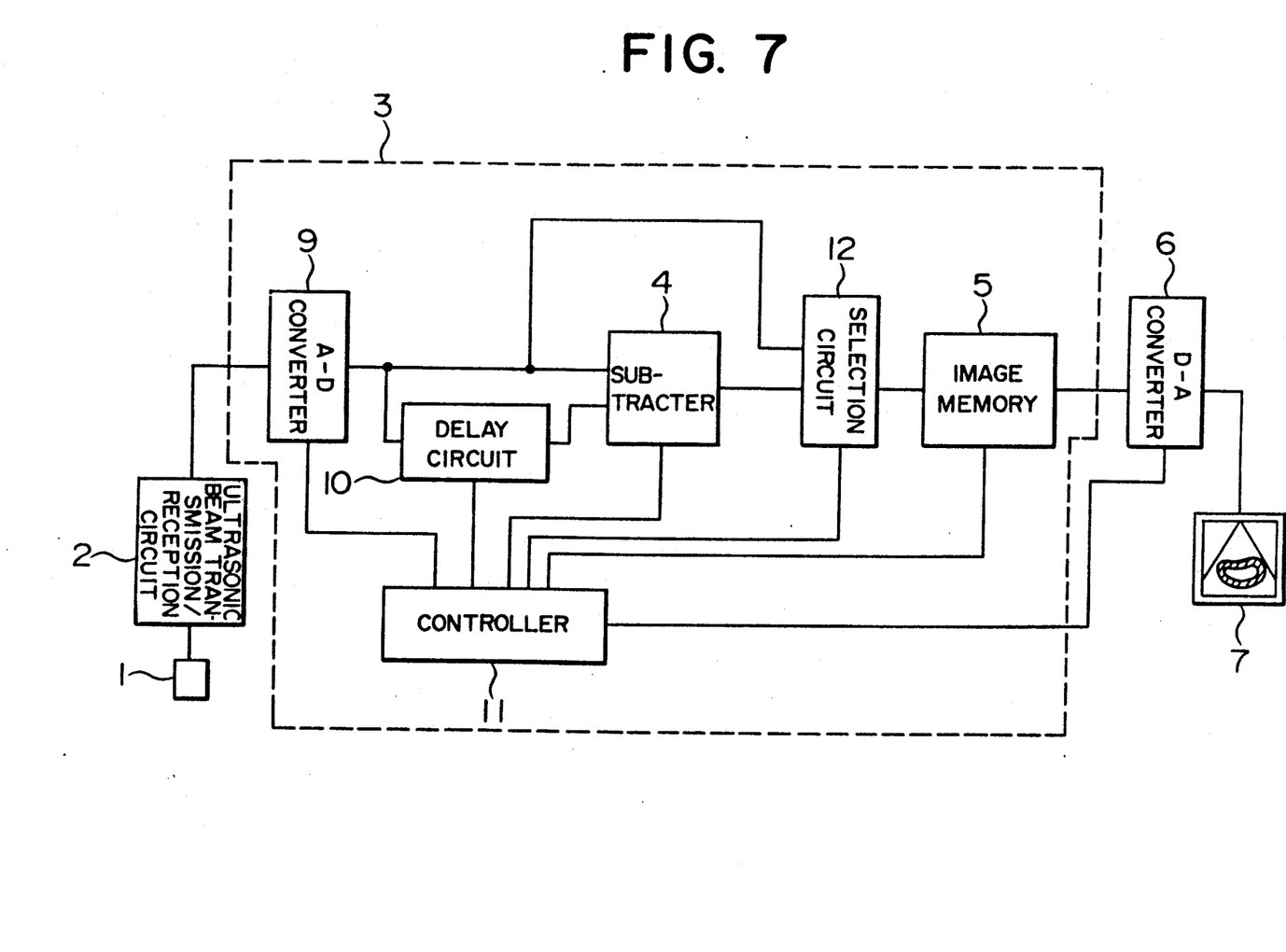
FIG. 7 is a block diagram showing a third embodiment of the present invention.

FIG. 7 is a block diagram showing a third embodiment of the present invention. In the third embodiment, a difference from the first embodiment shown in FIG. 1 is that between the subtracter 4 and the image memory, there is additionally provided a selection circuit 12 for receiving tomographic image data from the A-D converter 9 and the subtraction image data from the subtracter 4, and for selecting either the tomographic image data or the subtraction image data in synchronism with the display intervals, and for outputting selected image data. In the third embodiment, by using image data from the selection circuit 12, a tomographic image and a subtraction image are displayed simultaneously in the same picture of the image display 7.

In this case, the tomographic image data from the A-D converter 9 and the subtraction image data calculated by the subtracter 4 are input to the selection circuit 12, and the tomographic image data or the subtraction image data is selectively output by the selection circuit 12. More specifically, with regard to the image data which is supplied, while ultrasonic scanning is being performed to obtain data for one frame, the selection circuit 12 switches over the image data so as to output the tomographic image data in some time slot and output the subtraction image data in other time slot. The image data sequentially selected and output as described are written in the image memory subsequent to the selector circuit 12. The image data read out from the image memory 5 under control by the controller 11 is converted into an analog signal by the D-A converter 6, and then, supplied to the image display 7 and displayed. At this time, a tomographic image Ia and a subtraction image Ib are shown on the same picture on the image display, those areas of which are divided by optional ultrasonic scanning lines $l_1$ and $l_2$, as shown in FIG. 8, for example. It is possible to perform two-time successive transmission and reception according to the present invention as shown in FIGS. 2 and 5 only in the area defined by the scanning lines $l_1$ and $l_2$, and perform one-time successive transmission and reception in the other areas. This method can prevent the frame rate from decreasing, and can be applied to the second embodiment in FIG. 4.

Figure 9:
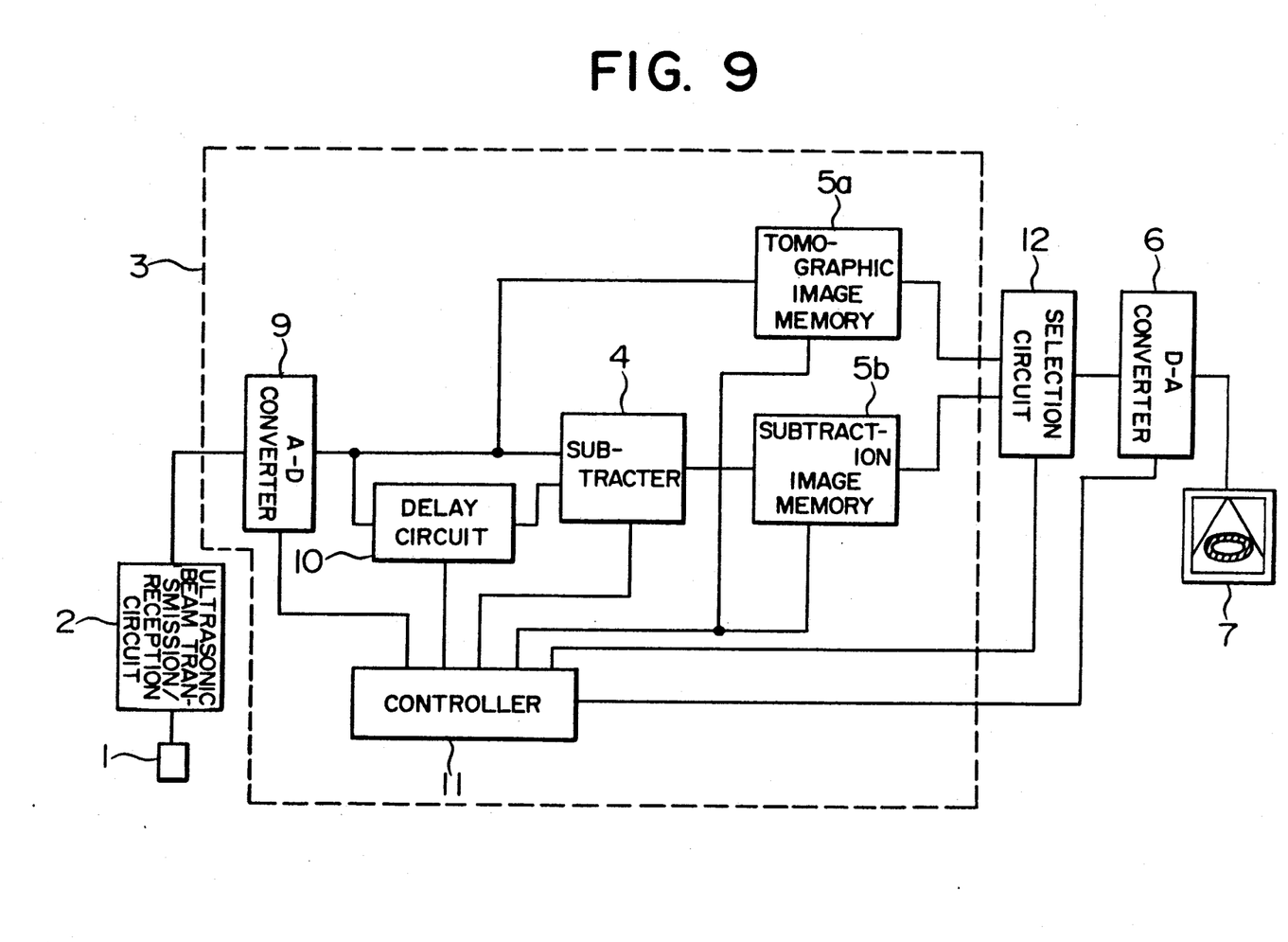
FIG. 9 is a block diagram showing a fourth embodiment of the present invention.

FIG. 9 is a block diagram showing a fourth embodiment of the present invention. The fourth embodiment differs from the first embodiment in FIG. 1 in that there are additionally provided in the DSC 3 a tomographic image memory 5a for storing tomographic image data supplied from the A-D converter 9 and a subtraction image memory 5b, connected to the output side of the subtracter 4, for storing subtraction image data supplied from the subtracter 4, and that a selection circuit 12 is also provided, which is connected to the output sides of those memories 5a and 5b. The tomographic image memory 5a and the subtraction image memory 5b operate such that image data are written at intervals of the ultrasonic beam transmission and reception under control by the controller 11, and the image data are read out at output intervals of the image display devices 6 and 7.

Figure 10A:
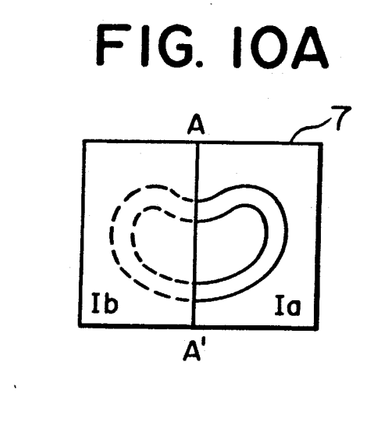
FIGS. 10A, 10B and 10C are explanatory diagrams showing examples of image display in the fourth embodiment.
Figure 10B:
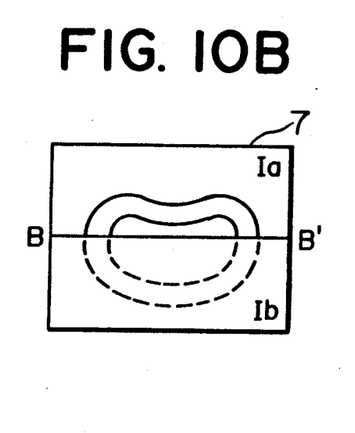
Figure 10C:
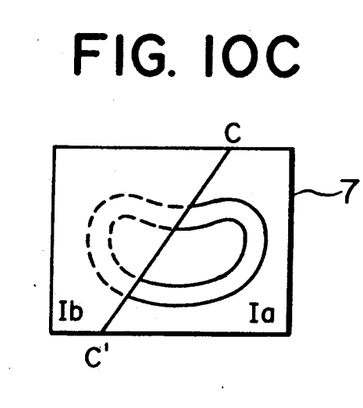

Next, the operation of the fourth embodiment arranged as above mentioned will be described with reference to FIGS. 10A to 10C. In the manner shown in FIG. 1, tomographic image data output from the A-D converter 9 in the DSC 3 is sent to the subtracter 4 and the image memory 5a for the tomographic images. The subtracter 4 performs an arithmetic operation as described above and generates subtraction image data, then sends it to the subtraction image memory 5b. In the tomographic image memory 5a and the subtraction image memory 5b, image data is written under control by the controller 11 so that a frame of the tomographic image and a frame of the subtraction image are formed by the line data and the subtraction data obtained by scanning in the same scanning directions. Then, from the tomographic image memory 5a and the subtraction image memory 5b in which image data has been written as described, the tomographic image data and the subtraction image data are read out, and input into the selection circuit 12. The selection circuit 12 selects and output the tomographic image data or the subtraction image data in synchronism with the display intervals of the image display 7. For timing the switch-over between the tomographic image data and the subtraction image data by the selection circuit 12, one method is to switch over the image data at a time phase corresponding to a line A—A' in the vertical direction, for example, during horizontal scanning of the image display 7 as shown in FIG. 10A. A second method is to switch over the image data at a time phase corresponding to a line B—B' in the horizontal direction as shown in FIG. 10B. A third method is to switch over the image data at a time phase corresponding to a line C—C' in a diagonal direction by combining the above-mentioned two methods as shown in FIG. 10C. Consequently, as shown in FIGS. 10A, 10B, and 10C, the tomographic images Ia are shown on one side and the subtraction images Ib are shown on the other side in the same picture simultaneously, those two areas being divided by optional line segments A—A', B—B', and C—C' of the image display 7. These methods can be applied to the second embodiment shown in FIG. 4.

Figure 11:
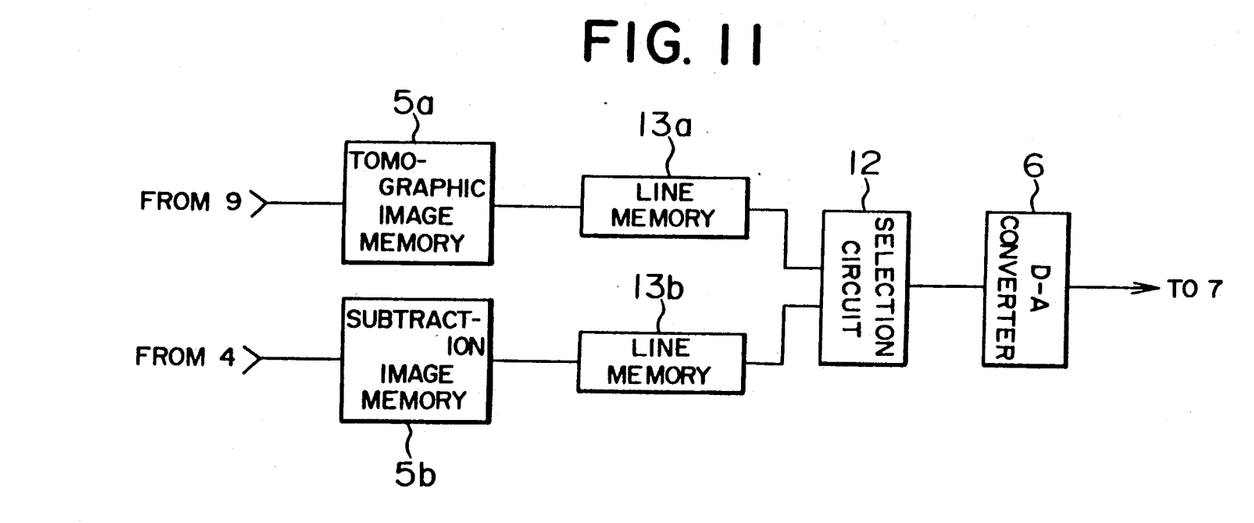
FIG. 11 is a fifth embodiment of the present invention.
Figure 12:
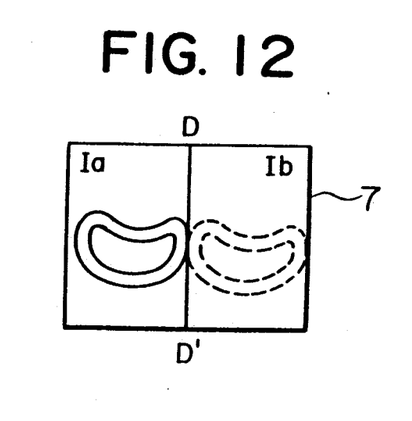
FIG. 12 is an explanatory diagram showing an example of image display in the fifth embodiment.

FIG. 11 is a block diagram showing the main components of a fifth embodiment of the present invention. The fifth embodiment differs from the fourth embodiment in FIG. 9 in that there are provided line memories 13a and 13b, each corresponding to data for one horizontal scanning line of the image display 7, the line memories 13a and 13b being located as a stage following those memories and preceding the selection circuit 12. In this case, the line memories 13a and 13b respectively store the tomographic image data and the subtraction image data, both corresponding to data for one horizontal scanning line, read from the tomographic image memory 5a and the subtraction image memory 5b. To read image data from the line memories 13a and 13b and display an image on the image display 7, by the operation of the selection circuit 12, image data from an optional location up to a location corresponding to a half of one horizontal scanning line of the image display 7 is output from the first line memory 13a, and subsequently, image data of a section corresponding to the same read out section of the first line memory 13a is output from the second line memory 13b in which subtraction image is stored. Those tomographic image data and subtraction image data are passed through the D-A converter 6 and are displayed on the image display 7. In this process, the controller 11 controls so that tomographic image data is displayed in the former half, for example, of a horizontal scanning period and subtraction image data is displayed in the latter half of that period. As a result, as shown in FIG. 12, the picture of the image display 7 is divided into two, left and right areas, and a tomographic image Ia is shown in one half area and side by side with this image, a subtraction image Ib of the same time phase is shown in the other half area.

Figure 13:
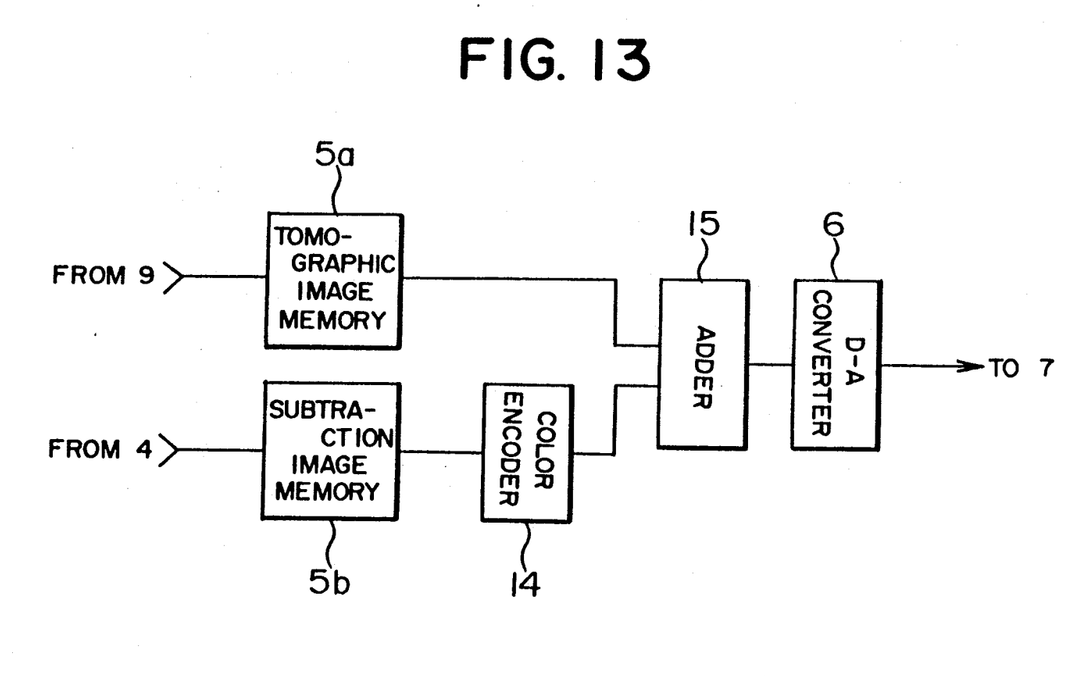
FIG. 13 is a block diagram of the main components showing a sixth embodiment of the present invention.

FIG. 13 is a block diagram of the main components showing a sixth embodiment of the present invention. The sixth embodiment differs from the fourth embodiment in FIG. 9 in that there is provided a color encoder 14 for converting subtraction image data into color information comprising R, G and B signals at a stage following the subtraction image memory 5b, and in place of the selection circuit 12 above mentioned, there is also provided an adder 15, on the output side of both the color encoder 14 and the tomographic image memory 5a, for superposing the tomographic image data on the subtraction image data. In this case, subtraction image data colored by the color encoder is superposed on tomographic image data supplied from the tomographic image memory 5a encoder 14. The combined data is sent to the image display 7, and a color image is displayed. Therefore, a color subtraction image is shown superposed on a monochrome tomographic image, so that the state of an abnormal locomotive region can be recognized more easily.

What is claimed is:

1. An image forming method in an ultrasonic diagnostic apparatus, comprising the steps of;
    (a) performing two successive transmissions and receptions of an ultrasonic beam in a scanning direction during intervals shorter than a frame period, in an ultrasonic diagnostic apparatus for scanning by sequentially changing a scanning direction in a specified scanning area of an examined body, said transmission and reception made earlier being defined as a first transmission and reception, said transmission and reception made later being defined as a second transmission and reception;
    (b) obtaining subtraction image data from a difference calculated between line data obtained by the first transmission and reception and line data obtained by the second transmission and reception; and
    (c) displaying a subtraction image formed by said subtraction image data in a specified area on an image display.

2. An image forming method according to claim 1, wherein said step of performing two successive transmissions and receptions of the ultrasonic beam, includes a step of performing said ultrasonic beam transmission and reception once in a first area and performing said ultrasonic beam transmission and reception twice in a second area of said scanning area.

3. An image forming method according to claim 1, wherein said step of obtaining said subtraction image data further comprises:
    delaying line data, obtained by the first transmission and reception, for a specified time; and
    obtaining said subtraction image data from a difference between said line data delayed and said line data obtained by the second transmission and reception.

4. An image forming method according to claim 3, wherein said delaying step includes a step of setting said specified delay time to an integer multiple of time required for one-time transmission and reception.

5. An image forming method according to claim 1, wherein said transmission and reception of an ultrasonic beam twice in a scanning direction is performed in every scanning direction over a scanning area.

6. An image forming method in an ultrasonic diagnostic apparatus, comprising the steps of:
    (a) performing two times of transmission and reception of an ultrasonic beam in the same scanning direction at shorter intervals than a frame rate, in an ultrasonic diagnostic apparatus for scanning by sequentially changing a scanning direction in a specified scanning area of an examined body, said transmission and reception made earlier being defined as a first transmission and reception, said transmission and reception made later being defined as a second transmission and reception;
    (b) obtaining subtraction image data from a difference calculated between line data obtained by the second transmission and reception; and
    (c) displaying a subtraction image formed by said subtraction image data in a specified area on an image display, wherein said display step includes a step of displaying a tomographic image formed by line data obtained by one-time of said transmission and reception of the ultrasonic beam and said subtraction image simultaneously.

7. An image forming method according to claim 6, wherein said display step includes a step of displaying said subtraction image in color.

8. An image forming method according to claim 6, wherein said displaying step comprises a step of displaying a single image which is formed with said tomographic image and said subtraction image.

9. An image forming method according to claim 6, wherein said displaying step comprises a step of displaying separate images, each is formed either with said tomographic image or said subtraction image.

10. An ultrasonic diagnostic apparatus comprising:
    (1) an ultrasonic beam transmission and reception unit for transmitting and receiving an ultrasonic beam to and from an examined body;
    (2) a scanner for scanning a specified scanning area of said examined body by sequentially changing a scanning direction of said ultrasonic beam;
    (3) a scanning control unit for controlling said scanning means so that said ultrasonic beam transmission and reception is made two successive times in a scanning direction at intervals shorter than a frame period, said transmission and reception made earlier is defined as a first transmission and reception, said transmission and reception made later being defined as a second transmission and reception;
    (4) a delay circuit for delaying line data obtained by the first transmission and reception for a specified time;
    (5) a subtracter for obtaining subtraction image data from a difference between said delayed line data and said line data obtained by the second transmission and reception;
    (6) an image memory for forming an image from said subtraction image data and for storing said image; and
    (7) an image display for displaying said image formed.

11. An ultrasonic diagnostic apparatus according to claim 10, wherein said scanning control unit includes control unit for performing said ultrasonic beam transmission and reception once in a first area and twice in a second area of said scanning area.

12. An ultrasonic diagnostic apparatus according to claim 10, wherein said transmission and reception of an ultrasonic beam twice in a scanning direction is performed in every scanning direction over a scanning area.

13. An ultrasonic diagnostic apparatus comprising:

(1) ultrasonic beam transmission and reception means for transmitting and receiving an ultrasonic beam to and from an examined body;

(2) scanning means for scanning a specified scanning area of said examined body by sequentially changing the scanning direction by said ultrasonic beam transmission and reception means;

(3) scanning control means for controlling said scanning means so that said ultrasonic beam transmission and reception is made twice in the same scanning direction at shorter intervals than the frame rate, said transmission and reception made earlier is defined as a first transmission and reception, said transmission and reception made later being defined as a second transmission and reception;

(4) means for delaying said line data obtained by the first transmission and reception for a specified time;

(5) means for obtaining subtraction image data from a different between said delayed line data and said line data obtained by the second transmission and reception;

(6) image memory means for forming an image from said subtraction image data and for storing said image; and (7) image display means for displaying said image formed, wherein said scanning control means includes control means for performing the second transmission and reception immediately after the first transmission and reception is made.

14. An ultrasonic diagnostic apparatus comprising:

(1) ultrasonic beam transmission and reception means for transmitting and receiving an ultrasonic beam to and from an examined body;

(2) scanning means for scanning a specified scanning area of said examined body by sequentially changing the scanning direction by said ultrasonic beam transmission and reception means;

(3) scanning control means for controlling said scanning means so that said ultrasonic beam transmission and reception is made twice in the same scanning direction at shorter intervals than the frame rate, said transmission and reception made earlier is defined as a first transmission and reception, said transmission and reception made later being defined as a second transmission and reception;

(4) means for delaying said line data obtained by the first transmission and reception for a specified time;

(5) means for obtaining subtraction image data from a difference between said delayed line data and said line data obtained by the second transmission and reception;

(6) image memory means for forming an image from said subtraction image and for storing said image; and (7) image display means for displaying said image formed, further comprising selection means for selecting line data obtained by one-time of said transmission and reception of the ultrasonic beam or said subtraction image data and for outputting said selected data to said image memory means in synchronism with display intervals of said image display means, wherein said image memory means includes means for forming said image by a tomographic image formed by line data obtained by said one-time transmission and reception of the ultrasonic beam and a subtraction image obtained from said subtraction image data.

15. An ultrasonic diagnostic apparatus comprising:

(1) ultrasonic beam transmission and reception means for transmitting and receiving an ultrasonic beam to and from an examined body;

(2) scanning means for scanning a specified scanning area of said examined body by sequentially changing the scanning direction by said ultrasonic beam transmission and reception means;

(3) scanning control means for controlling said scanning means so that said ultrasonic beam transmission and reception is made twice in the same scanning direction at shorter intervals than the frame rate, said transmission and reception made earlier is defined as a first transmission and reception, said transmission and reception made later being defined as a second transmission and reception;

(4) means for delaying said line data obtained by the first transmission and reception for a specified time;

(5) means for obtaining subtraction image data from a difference between said delayed line data and said line data obtained by the second transmission and reception;

(6) image memory means for forming an image from said subtraction image data and for storing said image; and (7) image display means for displaying said image formed, further comprising: tomographic image memory means for storing tomographic image data obtained from line data obtained by said one-time of said transmission and reception of the ultrasonic beam;

means for reading said tomographic image data from said tomographic image memory means;

means for reading said subtraction image data from said image memory; and selection means for selecting said tomographic image data or said subtraction image data and for outputting selected image data to said image display in synchronism with display intervals of said image display means.

16. An ultrasonic diagnostic apparatus according to claim 13, further comprising:

tomographic image memory means for storing tomographic image data obtained from line data obtained by said one-time of said transmission and reception of the ultrasonic beam;

means for color-encoding said substraction image data output from said image memory means; and means for superposing said subtraction image data which has been color-encoded on said tomographic image data read from said tomographic image memory and for outputting said data superposed to said image display means.

17. An ultrasonic diagnostic apparatus according to claim 14, further comprising:

first memory means for storing said tomographic image data read from said tomographic image memory; and second memory means for storing said subtraction image data read from said image memory, wherein said selection means includes:

means for writing said tomographic image data read from the first memory means in an area corresponding to a half of one horizontal scanning line of said image display means; and means for writing said subtraction image data read from the second memory means in an area corresponding to a half of one horizontal scanning line of said image display means.

18. An ultrasonic diagnostic apparatus according to claim 16, wherein said selection means comprises means for constructing a single image with said tomographic image data and said subtraction image data.

19. An ultrasonic diagnostic apparatus according to claim 16, wherein said selection means comprises means for constructing separate images, each is formed either with said tomographic image data or said subtraction image data.

* * * * *